United States Patent
Yamamoto

(10) Patent No.: US 8,657,263 B2
(45) Date of Patent: Feb. 25, 2014

(54) DECONTAMINATION LIQUID SUPPLY DEVICE

(75) Inventor: Kanjun Yamamoto, Ishikawa-Ken (JP)

(73) Assignee: Shibuya Kogyo Co., Ltd., Kanazawa-shi, Ishikawa-ken (JP)

(*) Notice: Subject to any disclaimer, the term of this patent is extended or adjusted under 35 U.S.C. 154(b) by 483 days.

(21) Appl. No.: 12/932,684

(22) Filed: Mar. 3, 2011

(65) Prior Publication Data
US 2011/0309534 A1    Dec. 22, 2011

(30) Foreign Application Priority Data
Jun. 16, 2010  (JP) .................................. 2010/136827

(51) Int. Cl.
B01F 3/04    (2006.01)
(52) U.S. Cl.
USPC ........................................... 261/27; 261/64.1
(58) Field of Classification Search
USPC .............. 261/26, 27, 34.1, 62, 64.1
See application file for complete search history.

(56) References Cited

U.S. PATENT DOCUMENTS

| 2,970,821 | A | * | 2/1961 | Axt ................................. 261/16 |
| 6,325,359 | B1 | * | 12/2001 | Haga et al. ...................... 261/42 |
| 6,471,193 | B2 | * | 10/2002 | Cole Warren ................... 261/27 |
| 8,490,951 | B2 | * | 7/2013 | Feldstein et al. .................. 261/4 |

FOREIGN PATENT DOCUMENTS

JP    08-504612    5/1996

* cited by examiner

*Primary Examiner* — Charles Bushey
(74) *Attorney, Agent, or Firm* — Flynn, Thiel, Boutell & Tanis, P.C.

(57) ABSTRACT

A gas supply passage is connected to a decontamination liquid supply passage at a tail end portion side from a delivery device, and an on-off valve which opens and closes the gas supply passage is provided. A controller stores a housed weight of the decontamination liquid between a connection point at which the above described gas supply passage is connected to the decontamination liquid supply passage and the above described tail end portion. When a weight of the decontamination liquid is reduced by a total value of a predetermined weight W which should be supplied to the downstream side equipment and the above described housed weight as a result of starting supply of the decontamination liquid to the above described downstream side equipment, the controller opens the above described on-off valve to return the decontamination liquid at the upstream side from the connection point.

2 Claims, 4 Drawing Sheets

DECONTAMINATION LIQUID SUPPLY DEVICE

FIELD OF THE INVENTION

The present invention relates to a decontamination liquid supply device, and more particularly relates to a decontamination liquid supply device for supplying a decontamination liquid of a predetermined weight, such as a hydrogen peroxide solution, for example, to a sterilized gas generating apparatus or the like which generates a sterilized gas from the hydrogen peroxide solution.

DESCRIPTION OF THE PRIOR ART

There is conventionally known a decontamination liquid supply device which includes measuring means which measures the weight of the decontamination liquid stored in decontamination liquid storing means, a decontamination liquid supply passage with a tail end portion connected to the above described decontamination liquid storing means and downstream side equipment connected to a tip end portion, and delivery means which is provided midway in the decontamination liquid supply passage and supplies the decontamination liquid of the decontamination liquid storing means to the downstream side equipment, and supplies the decontamination liquid of a predetermined weight to the downstream side equipment via delivery means by measuring the weight of the decontamination liquid by the above described measuring means (Patent Document 1: National Publication of International Patent Application No. 8-504612).

In the decontamination liquid supply device, when a decontamination liquid of a predetermined weight is supplied to the downstream side equipment, an air purge operation of firstly eliminating the gas which remains between the delivery means and the tail end portion of the decontamination liquid supply passage connected to the above described decontamination liquid storing means, and filling the decontamination liquid supply passage with the decontamination liquid is required. After the decontamination liquid supply passage is filled with the decontamination liquid, the numeric value of the measuring means is reset to zero in this state, and subsequently, the decontamination liquid of the decontamination liquid storing means is supplied to the downstream side equipment by the delivery means while the weight of the decontamination liquid is being measured. Like this, according to the conventional device, the weight of the decontamination liquid which is supplied to the downstream side equipment can be measured from the decrease weight of the decontamination liquid which is measured by the measuring means.

However, in the conventional device, the air purge operation of eliminating the gas which remains between the delivery means and the tail end portion of the decontamination liquid supply passage which is connected to the above described decontamination liquid storing means is required prior to supply of the decontamination liquid as described above, and therefore, the operation thereof is complicated. Further, the air purge passage for this is required, and therefore, the structure is also complicated.

SUMMARY OF THE INVENTION

In view of the above circumstances, the present invention provides a decontamination liquid supply device which can eliminate the necessity of an air purge operation to enhance operability, and can simplify the structure as compared with the conventional devices.

More specifically, a first aspect of the present invention is a decontamination liquid supply device including measuring means which measures a weight of a decontamination liquid stored in decontamination liquid storing means, a decontamination liquid supply passage with a tail end portion connected to the decontamination liquid storing means and a tip end portion connected to downstream side equipment, and delivery means which is provided midway in the decontamination liquid supply passage and supplies the decontamination liquid of the decontamination liquid storing means to the downstream side equipment, and supplying the decontamination liquid of a predetermined weight to the downstream side equipment via the delivery means by measuring a weight of the decontamination liquid by the measuring means, wherein a gas supply passage for supplying a gas is connected to the decontamination liquid supply passage at a side of the tail end portion from the delivery means, an on-off valve which opens and closes the gas supply passage is provided, control means which receives a signal from the measuring means and controls opening and closing of the on-off valve is provided, the control means stores a housed weight of the decontamination liquid which is housed in the decontamination liquid supply passage between a connection point at which the gas supply passage is connected to the decontamination liquid supply passage and the tail end portion, and when a weight of the decontamination liquid is reduced by a total value of the predetermined weight and the housed weight as a result of starting supply of the decontamination liquid to the downstream side equipment, the control means opens the on-off valve to introduce the gas to the decontamination liquid supply passage, supplies the decontamination liquid at a downstream side from the connection point to the downstream side equipment, and returns the decontamination liquid at an upstream side from the connection point to the decontamination liquid storing means.

Further, a second aspect of the present invention is the decontamination liquid supply device, wherein the delivery means is a peristaltic pump.

According to the above described first aspect of the present invention, with the above described on-off valve opened, the above described control means can measure the weight of the decontamination liquid at that time based on the signal from the above described measuring means.

If the on-off valve is closed and the delivery means is actuated from this state, the decontamination liquid stored in the decontamination liquid storing means can be supplied to the downstream side equipment by the delivery means. When the weight of the decontamination liquid is decreased by the total value of the above described predetermined weight and housed weight as the decontamination liquid stored in the decontamination liquid storing means is supplied to the downstream side equipment, the control means opens the above described on-off valve to introduce a gas to the decontamination liquid supply passage.

In this state, the decontamination liquid at the downstream side from the above described connection point is supplied to the downstream side equipment, while the decontamination liquid at the upstream side from the connection point is returned to the decontamination liquid storing means.

In this manner, the decontamination liquid at the upstream side from the connection point is returned to the decontamination liquid storing means, and the weight of the returned decontamination liquid is the aforementioned housed weight. Therefore, the weight of the decontamination liquid supplied to the downstream side equipment corresponds to the predetermined weight which should be supplied to the downstream side equipment, as a result.

In this state, the above described on-off valve is in the opened state, and the control means can measure the weight of the decontamination liquid in this state based on the signal from the measuring means. Therefore, the control means closes the on-off valve from this state to actuate the delivery means, and thereby, the decontamination liquid of the predetermined weight can be supplied to the downstream side equipment as described above.

Consequently, according to the present invention, when the decontamination liquid of the predetermined weight is supplied to the downstream side equipment, an air purge operation as in the conventional devices is not required, and therefore, the operability can be enhanced as compared with the conventional devices. Further, an air purge passage is not required, and therefore, the structure can be simplified.

Furthermore, as in the above described second aspect of the present invention, a peristaltic pump which squeezes the decontamination liquid passage is adopted as the delivery means, and thereby, the decontamination liquid of the predetermined weight which is at the downstream side from the connection point after the on-off valve is opened can be reliably supplied to the downstream side equipment together with the introduced gas.

DETAILED DESCRIPTION OF THE EMBODIMENTS

Figure 1:
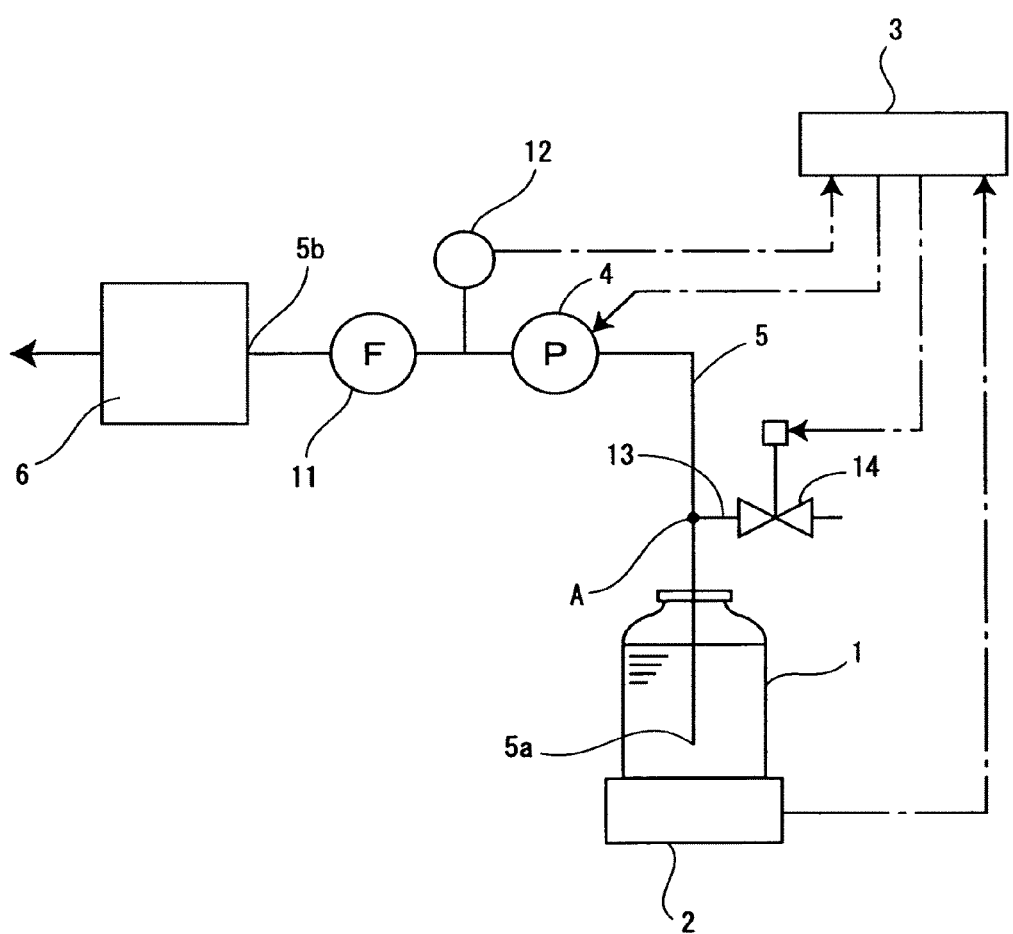
FIG. 1 is a circuit diagram showing one embodiment of the present invention.

Hereinafter, explaining the present invention with respect to the illustrated embodiment, in FIG. 1, a 35% hydrogen peroxide solution as a decontamination liquid is stored in a container 1 as decontamination liquid storing means, and the container 1 is placed on measuring means 2 such as an electronic force balance.

The measuring means 2 measures the weights of the container 1 and the decontamination liquid, and the signal of it is inputted in control means 3.

The decontamination liquid stored in the above described container 1 is supplied to downstream side equipment 6 via a decontamination liquid supply passage 5 by delivery means 4 such as a conventionally known peristaltic pump and other piston pumps. As the downstream side equipment 6, a sterilized gas generating device which evaporates the hydrogen peroxide solution to generate a sterilized gas is used, for example, when the decontamination liquid is a hydrogen peroxide solution.

The hydrogen peroxide solution in the container 1 is gradually supplied to the sterilized gas generating device as the downstream side equipment 6, and the hydrogen peroxide gas evaporated by the sterilized gas generating device is supplied as a sterilized gas to an inside of the equipment which requires sterilization such as an isolator.

The sterilized gas generating device may be of another type, for example, the one that generates a sterilized gas in a mist form by spraying a hydrogen peroxide solution by ultrasound.

A tail end portion 5a of the above described decontamination liquid supply passage 5 is connected to the above described container 1. More specifically, the above described tail end portion 5a is extended to a position close to a bottom portion of the container 1 so that the decontamination liquid stored in the container 1 can be sucked from the tail end portion 5a. Meanwhile, a tip end portion 5b of the decontamination liquid supply passage 5 is connected to the above described downstream side equipment 6.

The above described delivery means 4 is provided midway in the decontamination liquid supply passage 5, and a filter 11 for removing foreign matters is provided at a downstream side from the delivery means 4 in the decontamination liquid supply passage 5, and a pressure sensor 12 which detects a pressure in the decontamination liquid supply passage 5 is further provided between the filter 11 and the delivery means 4. By this pressure sensor 12, clogging of the above described filter 11 can be monitored, or an abnormality such as bending of the decontamination liquid supply passage 5 can be detected.

Further, a gas supply passage 13 which supplies a gas is connected to the decontamination liquid supply passage 5 at the side of the above described tail end portion 5a from the above described delivery means 4, and an on-off valve 14 which opens and closes the gas supply passage 13 is provided.

The decontamination liquid supply passage 5 in the portion where the above described gas supply passage 13 is connected is desirably disposed vertically downward, or to be inclined diagonally downward in order to return the decontamination liquid in the decontamination liquid supply passage 5 at the upstream side from a connection point A of the gas supply passage 13 into the container 1 as will be described in detail later.

The above described control means 3 receives a signal from the measuring means 2 as described above, and receives a signal from the above described pressure sensor 12, and can control drive of the delivery means 4 and opening and closing of the on-off valve 14.

The above described control means 3 is allowed to store a housed weight R of the decontamination liquid housed in the decontamination liquid supply passage 5 between the above described connection point A and the above described tail end portion 5a.

In the above configuration, in the state immediately before the decontamination liquid is supplied to the downstream side equipment 6, the delivery means 4 stops, and the on-off valve 14 is opened.

Figure 2:
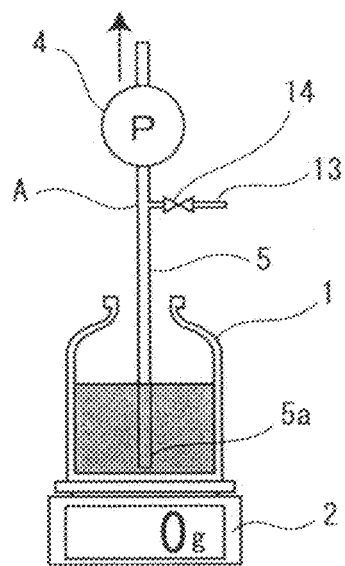
FIG. 2 is an explanatory view showing a state before a decontamination liquid is supplied to downstream side equipment.

In this state, as shown in FIG. 2, the liquid level height of the decontamination liquid in the decontamination liquid supply passage 5 in the container 1 corresponds to the liquid level height of the decontamination liquid in the container 1.

The control means 3 measures the total weight of the container 1 and the decontamination liquid by the measuring means 2, and when it is in the state immediately before supplying the decontamination liquid to the downstream side equipment 6, the control means 3 resets the weight and sets the weight to 0 g.

In the present embodiment, the description is made with a predetermined weight W which is supplied to the downstream side equipment 6 assumed to be 200 g, and the above described housed weight R assumed to be 5 g.

Figure 3:
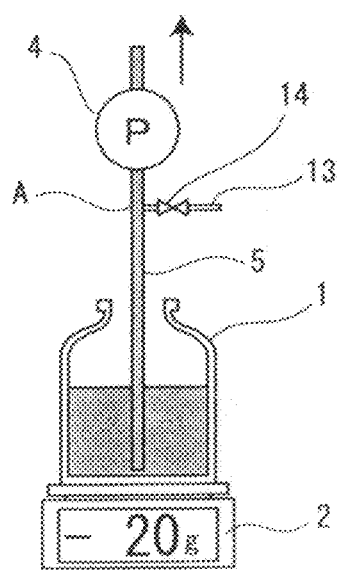
FIG. 3 is an explanatory view showing a state in which supply of the decontamination liquid is started.
Figure 4:
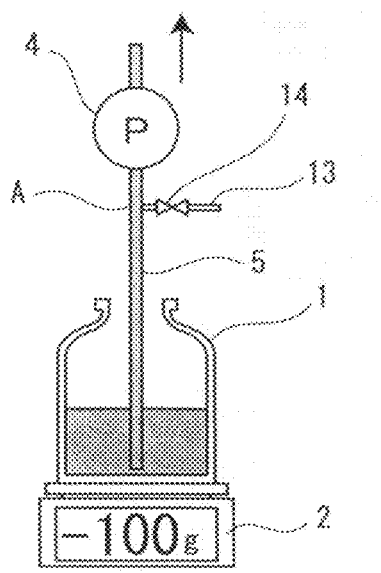
FIG. 4 is an explanatory view showing a state in which the decontamination liquid is being supplied.

When the decontamination liquid is supplied to the downstream side equipment 6, the control means 3 first closes the on-off valve 14, and actuates the delivery means 4. When the decontamination liquid in the container 1 is sucked into the decontamination liquid supply passage 5 as a result of this, the weight which is measured by the measuring means 2 is decreased with this (refer to FIGS. 3 and 4).

The decontamination liquid in the container 1 is supplied to the downstream side equipment 6 by a required amount through the decontamination liquid supply passage 5 and the filter 11 by an operation of the delivery means 4, and is evaporated by the sterilized gas generating device as the downstream side equipment 6.

Figure 5:
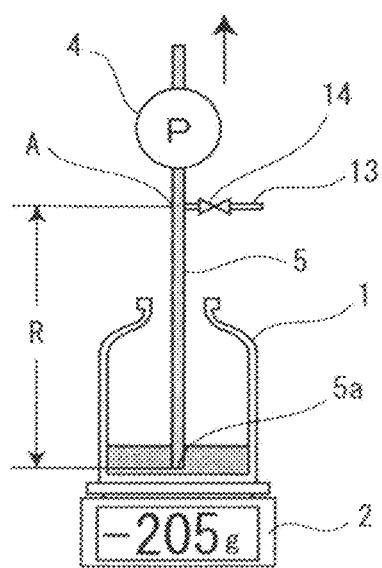
FIG. 5 is an explanatory view showing a state in which the weight of the decontamination liquid is decreased by a total value of a predetermined weight and a housed weight.

As shown in FIG. 5, when the decrease of the weight measured by the measuring means 2 becomes 205 g, that is, when the control means 3 detects that the decrease becomes the total value of the predetermined weight W which is supplied to the downstream side equipment 6 and the housed weight R, the control means 3 opens the above described on-off valve 14 to introduce air as a gas into the decontamination liquid supply passage 5.

Figure 6:
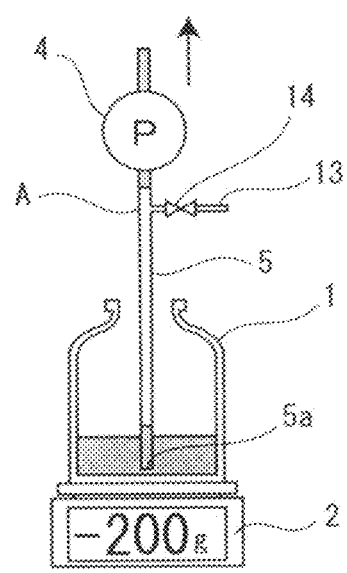
FIG. 6 is an explanatory view showing a state in which an on-off valve is opened.

In this state, the decontamination liquid at the downstream side from the above described connection point A is supplied to the downstream side equipment 6 by the delivery means 4, while the decontamination liquid at the upstream side from the connection point A is returned into the container 1, as shown in FIG. 6. When the decontamination liquid at the upstream side from the connection point A is returned into the container 1, the weight of the decontamination liquid which is supplied to the downstream side equipment 6 corresponds to 200 g which is the predetermined weight W which should be supplied to the downstream side equipment 6, since the weight of the returned decontamination liquid is 5 g of the aforementioned housed weight R.

When the decontamination liquid of 200 g which is the above described predetermined weight W is supplied to the downstream side equipment 6, the control means 3 stops operation of the delivery means 4, but in this state, the above described on-off valve 14 is in an opened state, and therefore, this state is the same as the aforementioned state immediately before the decontamination liquid is supplied to the downstream side equipment 6.

Accordingly, when the decontamination liquid of 200 g which is the above described predetermined weight W is newly supplied to the downstream side equipment 6 in succession, if the control means 3 resets the total weight of the container 1 and the decontamination liquid which is measured by the measuring means 2 and sets the weight to 0 g, the decontamination liquid of the predetermined weight W can be immediately supplied to the downstream side equipment 6 in the same manner as described above.

Meanwhile, when supply of the decontamination liquid to the downstream side equipment 6 is completed, the decontamination liquid in the above described decontamination liquid supply passage 5 is returned into the container 1, and therefore, the container 1 can be removed immediately. Alternatively, when the residual amount of the decontamination liquid in the container 1 runs short of the predetermined weight W, the container 1 can be replaced with a new container filled with the decontamination liquid.

What is claimed is:

1. A decontamination liquid supply device including measuring means which measures a weight of a decontamination liquid stored in decontamination liquid storing means, a decontamination liquid supply passage with a tail end portion connected to the decontamination liquid storing means and a tip end portion connected to downstream side equipment, and delivery means which is provided midway in the decontamination liquid supply passage and supplies the decontamination liquid of the decontamination liquid storing means to the downstream side equipment, and supplying the decontamination liquid of a predetermined weight to the downstream side equipment via the delivery means by measuring a weight of the decontamination liquid by the measuring means, wherein a gas supply passage for supplying: a gas is connected to the decontamination liquid supply passage at a side of the tail end portion from the delivery means, an on-off valve which opens and closes the gas supply passage is provided, control means which receives a signal from the measuring means and controls opening and closing of the on-off valve is provided, the control means stores a housed weight of the decontamination liquid which is housed in the decontamination liquid supply passage between a connection point at which the gas supply passage is connected to the decontamination liquid supply passage and the tail end portion, and when a weight of the decontamination liquid is reduced by a total value of the predetermined weight and the housed weight as a result of starting supply of the decontamination liquid to the downstream side equipment, the control means opens the on-off valve to introduce the gas to the decontamination liquid supply passage, supplies the decontamination liquid at a downstream side from the connection point to the downstream side equipment, and returns the decontamination liquid at an upstream side from the connection point to the decontamination liquid storing means.

2. The decontamination liquid supply device according to claim 1, wherein the delivery means is a peristaltic pump.

* * * * *